United States Patent [19]

Häfele et al.

[11] Patent Number: 5,901,397
[45] Date of Patent: May 11, 1999

[54] TOOTHBRUSH HAVING A BRUSH HOLDER MOVABLE AGAINST SPRING FORCE

[75] Inventors: Peter Häfele, Klagenfurt, Australia; Gerardus J. H. Roddeman, Son en Breugel, Netherlands; Arno Wolfger, Grafenstein, Austria

[73] Assignee: U.S. Philips Corporation, New York, N.Y.

[21] Appl. No.: 08/988,599

[22] Filed: Dec. 11, 1997

[30] Foreign Application Priority Data

Dec. 17, 1996 [AU] Australia ............................... 96890193

[51] Int. Cl.⁶ .................................................. A46B 13/02
[52] U.S. Cl. ............................................................ 15/22.1
[58] Field of Search .................................. 15/22.1, 22.2, 15/28, 167.1, 172

[56] References Cited

U.S. PATENT DOCUMENTS 5,253,382  10/1993  Beny ......................................... 15/22.2
5,467,494  11/1995  Müller et al. .

*Primary Examiner*—Randall E. Chin
*Attorney, Agent, or Firm*—Ernestine C. Bartlett

[57] ABSTRACT

In a toothbrush (1) comprising a stationary part (10) and a brush holder (24) which is movable with respect to the stationary part (10), and comprising a spring (48) which acts between the stationary part (10) and the brush holder (24), a link-motion device (49) is arranged between the stationary part (10) and the brush holder (24), in addition to the spring (48), in order to obtain a desired force characteristic, which link-motion device (49) is loaded by the spring (48) and comprises a link-motion follower (51) and a link-motion surface (50) having two link-motion surface portions (52, 53), the two link-motion surface portions (52, 53) adjoining one another by an edge-like transition portion (54).

6 Claims, 2 Drawing Sheets

5,901,397

TOOTHBRUSH HAVING A BRUSH HOLDER MOVABLE AGAINST SPRING FORCE

BACKGROUND OF THE INVENTION

The invention relates to a toothbrush comprising at least one stationary part, and a brush holder which is adapted to hold a brush and is movable with respect to the stationary part, and a spring which acts between the stationary part and the brush holder, and in which the brush holder can be held in a normal position by the spring force of the spring and in which the brush holder is movable into a deflection position against the spring force of the spring when a given limit value of the cleaning force exerted on the brush during operation of this brush is exceeded.

Such a toothbrush of the type defined in the opening paragraph is known, for example from the document EP 0 636 349 A1, which corresponds to U.S. Pat. No. 5,467,494, issued Nov. 21, 1995. In this known toothbrush the spring arranged between the stationary part and the brush holder is an angled blade spring of which one end portion is straight and fixedly connected to the stationary part and of which the other end portion is bent and cooperates with a stepped pressure surface of the brush holder at the location of the step of this holder. In this known toothbrush the limit value of the cleaning force, above which limit value the brush holder is movable into its deflection position against the spring force of the spring, is mainly determined by a threshold value of the spring force of the angled blade spring and also by the height of the step of the pressure surface and by the frictional conditions between the bent end portion of the blade spring and the pressure surface of the brush holder. However, the threshold value of the spring force depends comparatively strongly on the blade spring tolerances, which basically depend on the thickness of the blade spring, the magnitude of the blade spring angle and the shape of the bent end portion of the blade spring, and the frictional conditions between the bent end portion of the blade spring and the pressure surface of the brush holder are also dependent on tolerances and ageing. Owing to this fact, i.e. the comparatively strong influence of tolerances, the limit value of the cleaning force exerted on the brushes, for which the brush holder moves into its deflection position, exhibits a comparatively wide spread for different samples of the known toothbrush, which is undesirable.

SUMMARY OF THE INVENTION

It is an object of the invention to preclude the aforementioned problems and to provide an improved toothbrush of the type defined in the opening paragraph. To this end, according to the invention, a toothbrush of the type defined in the opening paragraph is characterized in that, in order to obtain a desired force characteristic, a link-motion device is arranged between the stationary part and the brush holder, in addition to the spring which acts therebetween, which link-motion device is loaded by the spring and comprises a link-motion surface and a link-motion follower, which are movable relative to one another, and the link-motion surface of the link-motion device comprises two link-motion surface portions, and the two link-motion surface portions adjoin one another by an edge-like transition portion. Thus, it is achieved that the limit value of the cleaning force exerted on the brush, above which value the brush holder is movable into its deflection position against the spring force of the spring, is mainly determined by the link-motion device, i.e. basically by the shape of that sliding-surface portion with which the link-motion follower cooperates before the brush holder moves into its deflection position, and by the edge-like transition portion between the two sliding-surface portions of the link-motion device. Since the link-motion device can be manufactured within very narrow tolerance limits, it is achieved in a simple manner that in a toothbrush in accordance with the invention the limit values of the cleaning force exerted on the brushes, at which the brush holder moves into its deflection position, lie very close to one another for different samples of a toothbrush in accordance with the invention, which is desired and advantageous.

In a toothbrush in accordance with the invention it has proved to be advantageous if the link-motion device comprises a slidably guided slider in which a cut-out has been provided, and the two link-motion surface portions of the link-motion surface of the link-motion device are formed by two bounding surface portions of the cut-out and the link-motion follower engages in the cut-out. This is advantageous for a simple and precise manufacture and construction of the link-motion device and, in addition, such a construction can be assembled in a simple manner.

In a toothbrush as defined in the preceding paragraph it has proved to be very advantageous if the slider is slidably guided on the stationary part, and the link-motion follower is stationarily mounted on the brush holder, and the spring is arranged between the stationary part and the slider. This is favorable in order to accommodate the link-motion device simply in such a toothbrush having the geometrical relations given in such a toothbrush.

It has further proved to be advantageous if the spring is formed by a helical tension spring. This is advantageous because such a tension spring is available with comparatively narrow tolerances.

In a toothbrush in accordance with the invention whose link-motion device comprises a slidably mounted slider, it has proved to be very advantageous if, for slidably guiding the slider, the slider has at least one slot in which a guide roller engages. This is advantageous in view of favorable frictional conditions for guiding the slider.

It has further proved to be advantageous if the link-motion follower comprises a rotatably mounted link-motion roller. This is advantageous for minimal frictional forces at the location where the sliding surface and the link-motion follower of the link-motion device cooperate with each other.

The above-mentioned as well as further aspects of the invention will become apparent from the embodiment described hereinafter by way of example and will be elucidated by means of this embodiment.

BRIEF DESCRIPTION OF THE DRAWINGS

The invention will now be described in more detail with reference to the drawings, which show an embodiment, given by way of example to which the invention is not limited.

DESCRIPTION OF THE PREFERRED EMBODIMENTS

Figure 1:
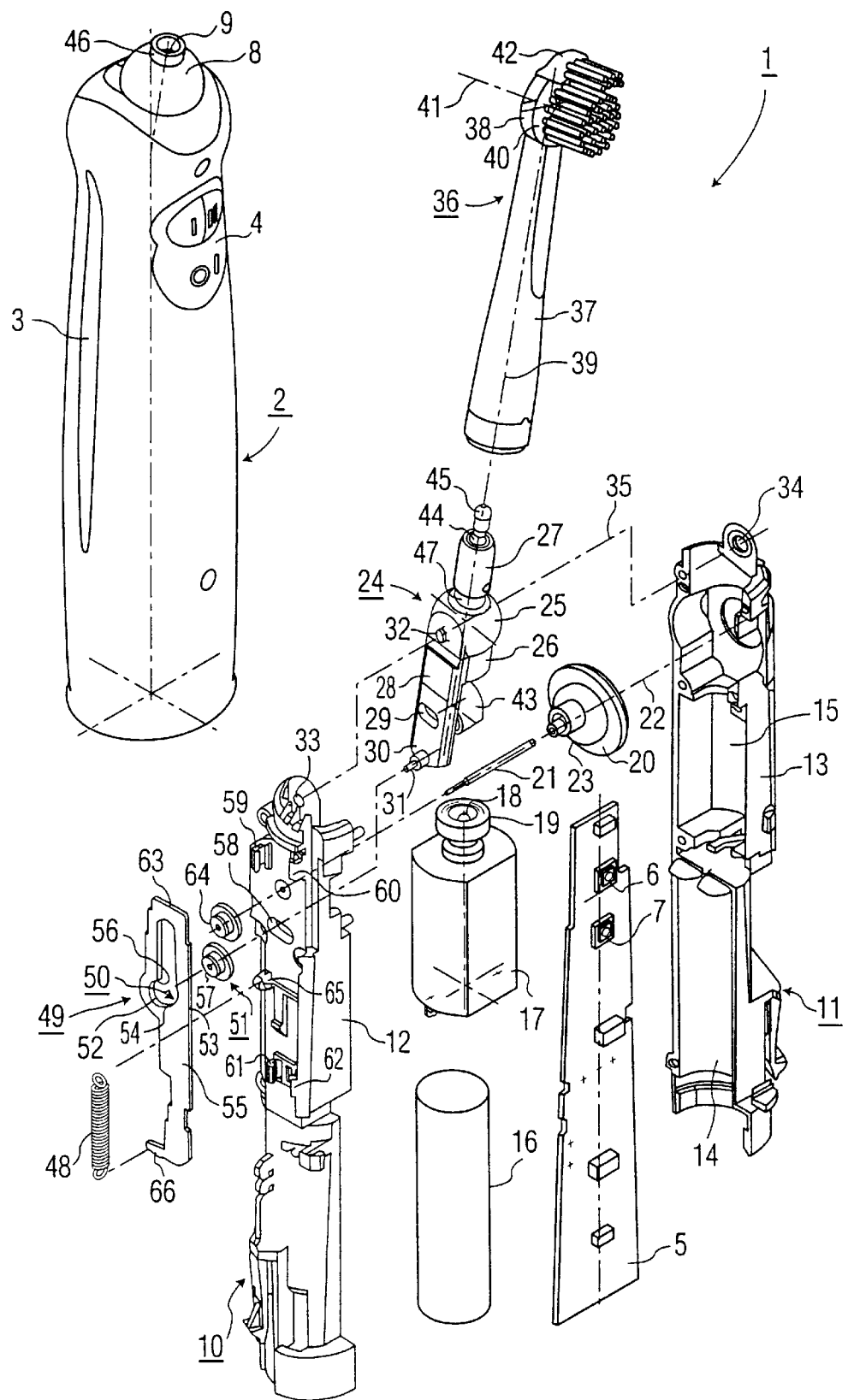
FIG. 1 is an exploded view of the relevant parts of a toothbrush in accordance with a possible embodiment of the invention, which toothbrush comprises a movable brush holder adapted to hold a brush.

FIG. 1 shows the relevant parts of a toothbrush 1 in accordance with the invention. The toothbrush 1 has a comparatively rigid plastic housing 2, which forms a grip member of the toothbrush 1. Connected to the housing 2 are two strip-shaped side grips, of which only one side grip 3 is visible in FIG. 1, an elastic plastic switch cover 5, which is integral with the housing 2 and underneath which two switches 6 and 7 on a printed circuit board 5 accommodated in the housing 2 are arranged, and an elastic plastic dome-shaped cover 8, which is also integral with the housing 2 and which has an opening 9, whose purpose will be described hereinafter, at its free end.

The housing 2 accommodates a first stationary support 10 and a second stationary support 11, both made of a rigid plastic. The two carrier parts 10 and 11 are connected in a manner not shown. The two carrier parts 10 and 11 each have a lateral surface 12 and 13, respectively. The printed circuit board 5 is mounted on the two lateral surfaces 12 and 13. The two carrier parts 10 and 11 each have two holder chambers, of which only a first holder chamber 14 and a second holder chamber 15 of the second carrier part 11 are visible in FIG. 1. In conjunction with the corresponding first holder chamber of the first carrier part 10 the first holder chamber 14 of the second carrier part 11 forms a holder space for a rechargeable battery 16, which can be charged via a charging circuit provided on the printed circuit board 5. In conjunction with the corresponding second holder chamber of the first carrier part 10 the second holder chamber 14 of the second carrier part 11 forms a holder space to accommodate an electric drive motor 17. In a manner not shown, the drive motor 17 is electrically connected to the printed circuit board 5 and can be energized by a power supply circuit on the printed circuit board 5, which circuit is powered by the battery 16.

The drive motor 17 has a drive shaft 18, which in the present case carries a pinion 19, which is locked in rotation to this shaft. A toothed wheel 20, shown only diagrammatically in FIG. 1, can be driven by the pinion 19. The toothed wheel 20 is mounted so as to be rotatable about an axis 22 by means of a spindle 21 mounted in the two stationary carrier parts 10 and 11. A hollow cylindrical eccentric part 23, which is disposed eccentrically relative to the axis 22, is integral with the toothed wheel 20.

The toothbrush 1 comprises a brush holder 24 which is movable relative to the first stationary carrier part 10 and also relative to the second stationary part 11. The brush holder 24 comprises a largely spherical portion 25 whose side facing the drive motor 17 is integrally connected to a substantially cylindrical portion 26 and whose side remote from the drive motor 17 is integrally connected to a substantially cylindrical coupling portion 27. The brush holder 24 further comprises an arm 28 connected to the spherical portion 25 and to the cylindrical portion 26. The arm 28 has a slot 29 to allow the passage of the spindle 21. The free end 30 of the arm 28 carries a trunnion 31, which is integral with the arm 28 and which projects laterally from the arm 28, the purpose of this trunnion being described hereinafter.

In the toothbrush 1 as shown in FIG. 1 the movable brush holder 24 is mounted so as to be pivotable relative to the two stationary carrier parts 10 and 11. For this purpose, the brush holder 24 comprises two trunnions, of which only one trunnion 32 is visible in FIG. 1. The visible first trunnion 32 engages a first bore 33 in the first carrier part 10. The non-visible trunnion engages a second bore 34 in the second carrier part 11. In this way, the brush holder 24 is mounted so as to be pivotable about an axis 35 relative to the two stationary carrier parts 10 and 11. The brush holder 24 is pivotable between a normal position, shown in FIG. 2A, and a deflection position, shown in FIG. 2B.

The brush holder 24 is adapted to hold a brush 36. The brush 36 comprises a tubular portion 37 and a disc portion 38 which is integrally connected to the tubular portion 37 at that end of the tubular portion 37 which is remote from the housing 2. The tubular portion 37 and the brush 36 have a longitudinal axis 39. A bristle holder 40 is mounted on the disc portion 37 so as to be movable, i.e. the brush holder 40 is reciprocatingly pivotable about a holder axis 41, which extends perpendicularly to the longitudinal axis 39, between two deflection positions through a center position.

Moreover, an interdental bristle holder 42 is mounted on the disc portion 38 so as to be movable, i.e. so as to be reciprocatingly movable transversely to the longitudinal axis 39 of the brush 36, and is coupled in driving engagement with the bristle holder 40 which is drivable for reciprocation along a circularly arcuate path, as a result of which the interdental bristle holder 41 is driven to reciprocate transversely to the longitudinal axis 39 of the brush 36 when the bristle holder 40 is reciprocated along the circularly arcuate path.

The bristle holder 40 is driven by the drive motor 17 via the afore-mentioned pinion 19, the toothed wheel 20 and the eccentric part 23. The eccentric part 23 engages in a slot formed in a block-shaped projection 43 of a connecting rod 44 and extending transversely to the longitudinal axis 39 of the brush 36. The connecting rod 44 is integral with the projection 43. The connecting rod 44 extends through a bore in the brush holder 24, which bore passes through the cylindrical portion 26, the spherical portion 25 and the cylindrical coupling portion 27.

When the brush 36 is mounted on the brush holder 24 the tubular portion 37 is suitably mechanically coupled to the cylindrical coupling portion 27 via a bayonet coupling, not shown. Furthermore, the cross-sectionally triangular free end 45 of the connecting rod 44 engages in a coupling recess in a driving rod, not shown, which is mounted in the tubular portion 37 so as to be movable substantially along the longitudinal axis 39. The end of the drive rod, not shown, which is remote from the connecting rod 444 is in driving engagement with the bristle holder 40 via a pivotal joint which is disposed eccentrically relative to the holder axis 41.

With respect to the construction of the brush 36 reference can be made to the currently non-published European Patent Application bearing the Application number 96 . . . , which corresponds to and claims the priority of the Applicants Austrian patent Application bearing the Application number A 2112/95, herewith incorporated by reference.

In the assembled condition of the toothbrush 1 the brush holder 24 extends with its cylindrical coupling portion 27 through the opening 9 in the cover 8 made of an elastic plastic, a hollow cylindrical portion 46 of the cover 8 being in sealing engagement with a cylindrical groove 47 of the coupling portion 27 of the brush holder 24 so as to preclude ingress of moisture or water into the housing interior.

Figure 2A:
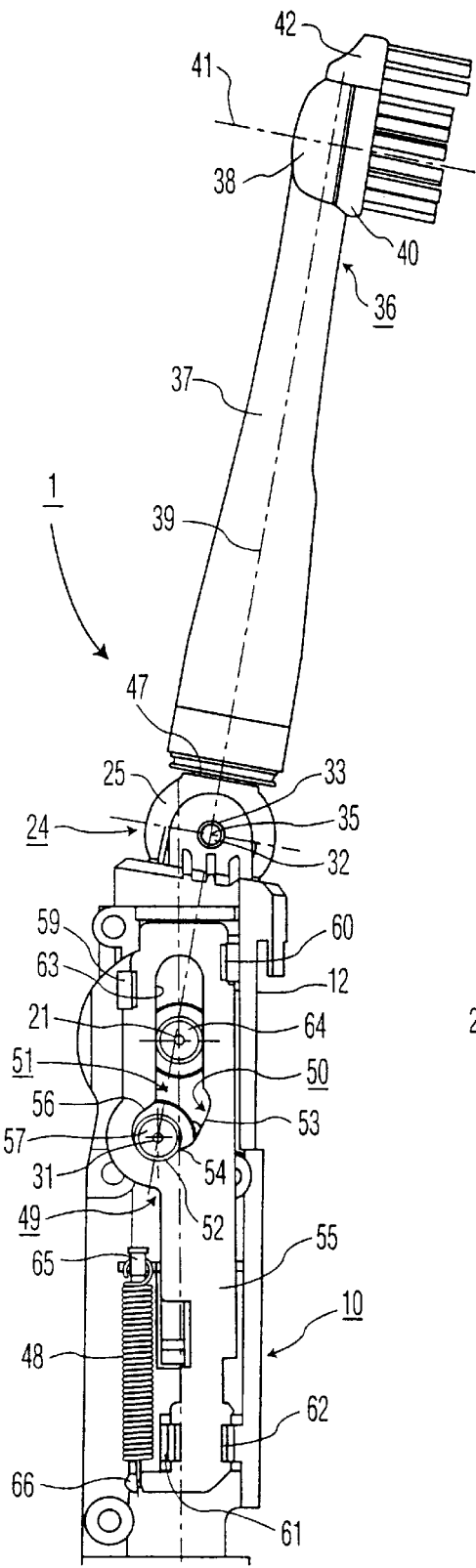
FIG. 2A is a diagrammatic side view showing a part of the brush holder and a brush held by this brush holder of the toothbrush shown in FIG. 1, the brush holder and the brush being in their normal position.
Figure 2B:
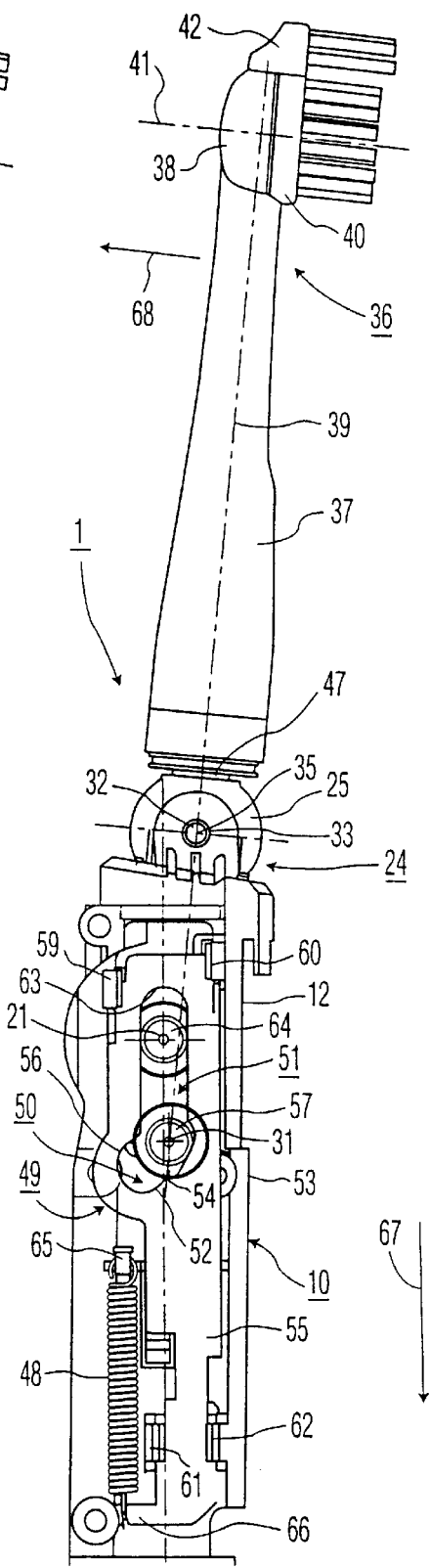
FIG. 2B, in the same way as FIG. 2A, shows a part of the brush holder and a brush held by this brush holder of the toothbrush shown in FIG. 1, the brush holder and the brush being in their deflection position.

As already stated hereinbefore, the brush holder 24 of the toothbrush 1, including the brush 36 it holds, is pivotable between a normal position, shown in FIG. 2A, and a deflection position, shown in FIG. 2B. In the toothbrush 1 a spring 48 has been provided, which spring is suitably formed by a helical tension spring acting between the first stationary carrier part 10 and the brush holder 24. The brush holder 24 can be held in its normal position by means of the spring force of the spring 48. When a given limit value of the cleaning force exerted on the brush 36 during operation is exceeded the brush holder 24, including the brush 36 held by it, is movable into its deflection position against the spring force of the spring 48.

In addition to the spring 48 acting between the stationary carrier part 10 and the brush holder 24 the toothbrush 1 advantageously comprises a link-motion device 49, which acts between said parts and is loaded by the spring 48, in order to obtain a desired force characteristic. The link-motion device 49 comprises a sliding surface 50 and a link-motion follower 51, which are movable relative to one another. Moreover, the sliding surface 50 of the link-motion 49 advantageously comprises two sliding-surface portions 52 and 53, i.e. a first sliding-surface portion 52 and a second sliding-surface portion 53, and the two sliding-surface portions 52 and 53 adjoin one another by an edge-like transition portion 54.

In an advantageous manner, the link-motion device 49 further comprises a slider 55 having a cut-out 56. In the present case, the two sliding-surface portions 52 and 53 of the sliding surface 50 of the link-motion device 49 are formed by two bounding surface portions of the cut-out 56. The link-motion follower 51 of the link-motion device 49 engages in the cut-out 56. The link-motion follower 51 comprises a rotatably mounted link-motion roller 57, which is rotatably mounted on the trunnion 31 of the brush holder 24, for which purpose the trunnion 31 is passed through a slot 58 formed for this purpose in the first carrier part 10. Thus, by means of the trunnion 31 the link-motion follower 51 is stationarily mounted on the brush holder 24 and is rotatable relative to the brush holder 24.

The slider 55 is retained on the first stationary carrier part 10 by means of four hooks 59, 60, 61 and 62 which project from the first carrier part 10. Thus, the slider is slidably guided on the first carrier part 10. for slidably guiding the slider 55 In the present case the slider 55 has a single slot 63 for slidably guiding the slider 55, which slot in the present case changes into the cut-out 56. The slot 63 is engaged by a guide roller 64, which is rotatably mounted on the spindle 21, which for this purpose extends through the first carrier part 10. In this way, the guide roller 64 is stationarily but rotatably mounted on the first carrier part 10. By means of the slot 63 and the guide roller 64 the slider 55 is guided with a comparatively low friction at the location of the sliding surface 50 and the link-motion roller 57. The slider 55 is guided so as to be slidable in its longitudinal direction by means of the two hooks 61 and 62 in the slider area which is remote from the slot 63. However, alternatively a guide roller which cooperates with a slot may be provided at this location, but this is not required owing to the comparatively large distance from the link-motion roller 57.

In the toothbrush 1 the spring 48 is arranged between the first stationary carrier part 10 and the slider 55. For this purpose the first stationary carrier part 10 comprises a coupling projection 65 and the slider 55 has a laterally projecting further coupling projection 66. The spring 58 is attached to both coupling projections 65 and 66. The spring 48 has a comparatively large spring length, a high initial spring tension, and a low stiffness, which results in a flat spring characteristic and, consequently, a substantially constant force over the entire operating range.

During normal operation of the toothbrush 1, when the cleaning force exerted on the brush 36 is below a given limit value—which is mainly determined by the link-motion device 49, i.e. essentially by the shape of the first sliding-surface portion 52, with which the link-motion roller 57 cooperates when the brush holder 24 is in its normal position, and by the edge-like transition portion 54 between the two sliding-surface portions 52 and 53 of the link-motion device 49 and, obviously, also by the spring force of the spring 48—the brush holder 24, together with the brush 36 it holds, is in the normal position shown in FIG. 2A, in that the spring 48 coupled to the first stationary carrier part 10 exerts an adequate force on the slider 55 of the link-motion device 49, as a result of which an adequate force is exerted on the link-motion roller 57 via first sliding-surface portion 52 which in this case cooperates with the link-motion roller 57 and, consequently, the link-motion roller 57 remains applied to the sliding-surface portion 52 and, as a result, the brush holder 24, together with the brush 36 it carries, is held in its normal position.

However, if during operation of the toothbrush 1 an excessive cleaning force, which exceeds the aforementioned limit value, is exerted on the brush 36, the link-motion roller 57 will exert such a large force on the first sliding-surface portion 52 that the link-motion roller 57 is moved past the edge-like transition portion 54 between the two sliding-surface portions 52 and 53, the slider 55 of the link-motion device 49 being moved in the direction indicated by the arrow 67 in FIG. 2B opposed by the force of the spring 48 and, at the same time, the brush holder 24 and the brush 36 carried by this holder being moved into its deflection position in the direction indicated by the arrow 68 which is also shown in FIG. 2B. In this way, the user is given a signal that he applies an excessive cleaning force.

When the applied excessive cleaning force is reduced the slider 55 of the link-motion device 49 is moved from its operating position shown in FIG. 2A in a direction opposite to that indicated by the arrow 67 in FIG. 2B by the force of the spring 48, as a result of which the link-motion roller 57 again enters into operative engagement with the first sliding surface portion 52, causing the brush holder 24, and hence the brush 36 it carries, to be pivoted back into its normal position in a direction opposite to that indicated by the arrow 68 in FIG. 2B.

By providing the toothbrush described in the foregoing with the link-motion device in order to obtain a desired spring characteristic, which link-motion device can be manufactured within very narrow tolerance limits, it is achieved by simple means and in a simple manner that the movement of the brush holder into its deflection position takes place within very narrow tolerance limits of the cleaning force exerted on the brush, which is desired and advantageous.

The invention is not limited to the embodiment of a toothbrush in accordance with the invention as described hereinbefore. For example, a link-motion follower of a link-motion device, which is preferably formed by a link-motion roller, can also be arranged on the first stationary carrier part so as to be rotatable and this link-motion device can comprise a slider which is slidably guided on a pivotable brush holder and which has a cut-out whose bounding surfaces form the link-motion surface portions, the spring for loading this link-motion device being arranged between the pivotable brush holder and the slider which is guided so as to be slidable with respect to the pivotable brush holder. Moreover, it is possible to provide a further link-motion device which is guided so as to be slidable with respect to a pivotable brush holder and which has a cut-out whose bounding surfaces form the link-motion surface portions of the further link-motion device and, as link-motion follower of this further link-motion device, a link-motion roller mounted on the first stationary carrier part so as to be movable in the longitudinal direction of the carrier part and so as to be rotatable, one end of the spring now acting on the first stationary carrier part and the other end on the movably supported link-motion roller.

We claim:

1. A toothbrush comprising at least one stationary part, and a brush holder which is adapted to hold a brush and is movable with respect to the stationary part, and a spring which acts between the stationary part and the brush holder, and in which the brush holder can be held in a normal position by the spring force of the spring and in which the brush holder is movable into a deflection position against the spring force of the spring when a given limit value of the cleaning force exerted on the brush during operation of this brush is exceeded, characterized in that, in order to obtain a desired force characteristic, a link-motion device is arranged between the stationary part and the brush holder, in addition to the spring which acts therebetween, which link-motion device is loaded by the spring and comprises a link-motion surface and a link-motion follower, which are movable relative to one another, and the link-motion surface of the link-motion device comprises two link-motion surface portions, and the two link-motion surface portions adjoin one another by an edge-like transition portion.

2. A toothbrush as claimed in claim 1, wherein the link-motion device comprises a slidably guided slider in which a cut-out has been provided, and the two link-motion surface portions of the link-motion surface of the link-motion device are formed by two bounding surface portions of the cut-out and the link-motion follower engages in the cut-out.

3. A toothbrush as claimed in claim 2, wherein the slider is slidably guided on the stationary part, and the link-motion follower is stationarily mounted on the brush holder, and the spring is arranged between the stationary part and the slider.

4. A toothbrush as claimed in claim 3, wherein the spring is a helical tension spring.

5. A toothbrush as claimed in claim 2, for slidably guiding the slider, the slider has at least one slot in which a guide roller engages.

6. A toothbrush as claimed in claim 1, wherein the link-motion follower comprises a rotatably mounted link-motion roller.

* * * * *